US007531471B2

(12) United States Patent
    Quincy, III

(10) Patent No.: US 7,531,471 B2
(45) Date of Patent: May 12, 2009

(54) SUBSTRATE CONTAINING A DEODORIZING INK

(75) Inventor: Roger B. Quincy, III, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 285 days.

(21) Appl. No.: 11/700,239

(22) Filed: Jan. 30, 2007

(65) Prior Publication Data

US 2008/0179562 A1    Jul. 31, 2008

(51) Int. Cl.
    B32B 5/18    (2006.01)
    A61L 9/04    (2006.01)
(52) U.S. Cl. .................................... 442/375; 523/102
(58) Field of Classification Search ................ 442/375; 428/143, 220, 317.9, 318.4; 523/102
    See application file for complete search history.

(56) References Cited

U.S. PATENT DOCUMENTS

| | | | |
|---|---|---|---|
| 2,593,146 A | 4/1952 | Leigh et al. |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,069,297 A | 1/1978 | Saito et al. |
| 4,285,343 A | 8/1981 | McNair |
| 4,285,831 A | 8/1981 | Yoshida et al. |
| 4,307,143 A | 12/1981 | Meitner |
| 4,340,563 A | 7/1982 | Appel et al. |
| 4,341,216 A | 7/1982 | Obenour |
| 4,427,836 A | 1/1984 | Kowalski et al. |
| 4,468,498 A | 8/1984 | Kowalski et al. |
| 4,488,969 A | 12/1984 | Hou |
| 4,525,410 A | 6/1985 | Hagiwara et al. |
| 4,594,363 A | 6/1986 | Blankenship et al. |
| 4,608,047 A | 8/1986 | Mattingly |
| 4,677,019 A | 6/1987 | von Blücher |
| 4,687,478 A | 8/1987 | Van Tilburg |
| 4,707,398 A | 11/1987 | Boggs |
| 4,758,239 A | 7/1988 | Yeo et al. |
| 4,783,220 A | 11/1988 | Gamble et al. |
| 4,797,318 A | 1/1989 | Brooker et al. |
| 4,802,473 A | 2/1989 | Hubbard et al. |
| 4,880,842 A | 11/1989 | Kowalski et al. |
| 4,886,512 A | 12/1989 | Damico et al. |
| 4,950,264 A | 8/1990 | Osborn, III |
| 4,969,457 A | 11/1990 | Hubbard et al. |
| 4,988,505 A | 1/1991 | Watanabe et al. |
| 5,009,653 A | 4/1991 | Osborn, III |
| 5,020,533 A | 6/1991 | Hubbard et al. |
| 5,037,412 A | 8/1991 | Tanzer et al. |
| 5,085,654 A | 2/1992 | Buell |
| 5,122,418 A | 6/1992 | Nakane et al. |
| 5,157,084 A | 10/1992 | Lee et al. |
| 5,190,563 A | 3/1993 | Herron et al. |
| 5,197,959 A | 3/1993 | Buell |
| 5,267,992 A | 12/1993 | Van Tilburg |
| 5,308,346 A | 5/1994 | Sneller et al. |
| 5,322,061 A | 6/1994 | Brunson |
| 5,342,342 A | 8/1994 | Kitaoka |
| 5,342,876 A | 8/1994 | Abe et al. |
| 5,360,827 A | 11/1994 | Toda et al. |
| 5,382,400 A | 1/1995 | Pike et al. |
| 5,383,450 A | 1/1995 | Hubbard et al. |
| 5,407,442 A | 4/1995 | Karapasha |
| 5,429,628 A | 7/1995 | Trinh et al. |
| 5,480,636 A | 1/1996 | Maruo et al. |
| 5,486,356 A | 1/1996 | Yim |
| 5,494,971 A | 2/1996 | Blankenship |
| 5,509,914 A | 4/1996 | Osborn, III |
| 5,521,008 A | 5/1996 | Lieberman et al. |
| 5,521,253 A | 5/1996 | Lee et al. |

(Continued)

FOREIGN PATENT DOCUMENTS

| | | |
|---|---|---|
| EP | 0 483500 A1 | 5/1992 |
| EP | 1 108406 A2 | 6/2001 |
| EP | 1 108406 A3 | 6/2001 |
| EP | 1 125543 A2 | 8/2001 |
| EP | 1 125543 A3 | 8/2001 |
| WO | WO 9900093 A1 | 1/1999 |
| WO | WO 9945099 A1 | 9/1999 |
| WO | WO 0025660 A1 | 5/2000 |
| WO | WO 0065083 A2 | 11/2000 |
| WO | WO 0065083 A3 | 11/2000 |

(Continued)

OTHER PUBLICATIONS

Article—*Adsorption of Gases in Multimolecular Layers*, Brunauer et al., The Journal of American Chemical Society, vol. 60, Feb. 1938, pp. 309-319.

(Continued)

*Primary Examiner*—Lynda Salvatore
(74) *Attorney, Agent, or Firm*—Dority & Manning, P.A.

(57) ABSTRACT

A substrate that contains a deodorizing ink is provided. The composition contains carbonaceous particles (e.g., activated carbon) for adsorbing one or more malodorous compounds to reduce odor. Because carbonaceous particles typically have a dark black color that is sometimes aesthetically displeasing to the user, the deodorizing ink of the present invention also contains voided synthetic particles that mask, at least to some extent, the darker carbonaceous particles. More specifically, the voids of the particles contain air, which can scatter or diffract light to create an opaque effect that may hide the black color of the carbonaceous particles. In this manner, the color presented to the user may be more aesthetically pleasing.

32 Claims, No Drawings

U.S. PATENT DOCUMENTS

| | | |
|---|---|---|
| 5,540,916 A | 7/1996 | Parks |
| 5,553,608 A | 9/1996 | Reese et al. |
| 5,558,659 A | 9/1996 | Sherrod et al. |
| 5,561,167 A | 10/1996 | Matsumoto et al. |
| 5,569,234 A | 10/1996 | Buell et al. |
| 5,628,737 A | 5/1997 | Dobrin et al. |
| 5,634,916 A | 6/1997 | Lavon et al. |
| 5,649,916 A | 7/1997 | DiPalma et al. |
| 5,679,138 A | 10/1997 | Bishop et al. |
| 5,679,724 A | 10/1997 | Sacripante et al. |
| 5,693,385 A | 12/1997 | Parks |
| 5,702,378 A | 12/1997 | Widlund et al. |
| 5,716,349 A | 2/1998 | Taylor et al. |
| 5,813,398 A | 9/1998 | Baird et al. |
| 5,834,114 A | 11/1998 | Economy et al. |
| 5,836,932 A | 11/1998 | Buell et al. |
| 5,837,117 A | 11/1998 | Allegret |
| 5,855,999 A | 1/1999 | McCormack |
| 5,885,599 A | 3/1999 | Peterson et al. |
| 5,948,398 A | 9/1999 | Hanamoto et al. |
| 6,020,435 A | 2/2000 | Blankenship et al. |
| 6,057,072 A | 5/2000 | Guistina et al. |
| 6,096,299 A | 8/2000 | Guarracino et al. |
| 6,110,158 A | 8/2000 | Kielpikowski |
| 6,114,024 A | 9/2000 | Forte |
| 6,153,209 A | 11/2000 | Vega et al. |
| 6,186,991 B1 | 2/2001 | Roe et al. |
| 6,198,018 B1 | 3/2001 | Curro |
| 6,203,810 B1 | 3/2001 | Alemany et al. |
| 6,245,401 B1 | 6/2001 | Ying et al. |
| 6,358,499 B2 | 3/2002 | Hall-Puzio et al. |
| 6,358,537 B1 | 3/2002 | Hoshino et al. |
| 6,376,741 B1 | 4/2002 | Guarracino et al. |
| 6,427,693 B1 | 8/2002 | Blackstock et al. |
| 6,460,989 B1 | 10/2002 | Yano et al. |
| 6,479,146 B1 | 11/2002 | Caruso et al. |
| 6,479,150 B1 | 11/2002 | Liu et al. |
| 6,511,465 B1 | 1/2003 | Freiburger et al. |
| 6,517,906 B1 | 2/2003 | Economy et al. |
| 6,573,212 B2 | 6/2003 | McCrae et al. |
| 6,639,004 B2 | 10/2003 | Falat et al. |
| 6,663,611 B2 | 12/2003 | Blaney et al. |
| 6,740,406 B2 | 5/2004 | Hu et al. |
| 6,888,044 B2 | 5/2005 | Fell et al. |
| 2004/0060112 A1 | 4/2004 | Fell et al. |
| 2004/0122386 A1 | 6/2004 | Mocadlo |
| 2004/0122387 A1 | 6/2004 | Long et al. |
| 2004/0142041 A1 | 7/2004 | MacDonald et al. |
| 2004/0166248 A1 | 8/2004 | Hu et al. |
| 2004/0192148 A1 | 9/2004 | Kajander |
| 2005/0084412 A1 | 4/2005 | MacDonald et al. |
| 2005/0084438 A1 | 4/2005 | Do et al. |
| 2005/0084464 A1 | 4/2005 | McGrath et al. |
| 2005/0084632 A1 | 4/2005 | Urlaub et al. |
| 2005/0113771 A1 | 5/2005 | MacDonald et al. |
| 2006/0137568 A1 | 6/2006 | MacDonald et al. |
| 2006/0140902 A1 | 6/2006 | MacDonald et al. |
| 2006/0142709 A1 | 6/2006 | Quincy, III |
| 2006/0142828 A1 | 6/2006 | Schorr et al. |
| 2007/0026209 A1 | 2/2007 | MacDonald et al. |
| 2007/0100304 A1 | 5/2007 | Fell et al. |
| 2008/0147028 A1* | 6/2008 | Luna et al. .................. 604/359 |

FOREIGN PATENT DOCUMENTS

| | | |
|---|---|---|
| WO | WO 0065084 A2 | 11/2000 |
| WO | WO 0065084 A3 | 11/2000 |
| WO | WO 0065096 A1 | 11/2000 |
| WO | WO 0065347 A2 | 11/2000 |
| WO | WO 0065347 A3 | 11/2000 |
| WO | WO 0065348 A2 | 11/2000 |
| WO | WO 0065348 A3 | 11/2000 |

OTHER PUBLICATIONS

Article—*The Production of Materials and Chemical from Coal*, Derbyshire et al., American Chemical Society, Fuel Division, Preprints, vol. 39, 1994, pp. 113-120.

Article—*Activated Carbon in Dark Absorbent Articles* Lindsay et al., IP.Com, Aug. 9, 2001.

Search Report and Written Opinion for PCT/IB2008/050045 dated May 21, 2008.

Disclosure of U.S. Patent Application Form.

* cited by examiner

SUBSTRATE CONTAINING A DEODORIZING INK

BACKGROUND OF THE INVENTION

Odor control additives have been conventionally incorporated into substrates for a variety of reasons. For instance, absorbent articles may contain odor control additives to absorb compounds that result in the production of malodors contained in absorbed fluids or their degradation products. Examples of these compounds include fatty acids, ammonia, amines, sulfur-containing compounds, ketones and aldehydes. Various types of odor control additives have been employed for this purpose. For instance, activated carbon has been used to reduce a broad spectrum of odors. In spite of its excellent properties as an adsorbent, the use of activated carbon in disposable absorbent articles has been limited by its black color. Activated carbon granules may also make unwanted noise or provide an undesirable gritty feel when incorporated into an article worn against the body. In addition, many conventional techniques for forming activated carbon substrates are simply too complex and/or costly for consumer applications.

As such, a need currently exists for activated carbon substrates that have good physical properties and are capable of reducing odor. Further, a need also exists for an improved method of making such activated carbon substrates.

SUMMARY OF THE INVENTION

In accordance with one embodiment of the present invention, a substrate that contains a deodorizing ink is disclosed. The deodorizing ink comprises from about 10 wt. % to about 50 wt. % carbonaceous particles and from about 5 wt. % to about 40 wt. % voided synthetic particles. The voided synthetic particles have an average size less than the average size of the carbonaceous particles.

In accordance with another embodiment of the present invention, a nonwoven web that contains a deodorizing ink is disclosed. The deodorizing ink comprises from about 10 wt. % to about 50 wt. % activated carbon particles and from about 5 wt. % to about 40 wt. % voided latex particles. The carbonaceous particles have an average size of from about 5 to about 75 micrometers and the voided latex particles have an average size of about 5 micrometers or less.

Other features and aspects of the present invention are described in more detail below.

DETAILED DESCRIPTION OF REPRESENTATIVE EMBODIMENTS

Definitions

As used herein, the term "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth.

As used herein, the term "nonwoven web" refers to a web having a structure of individual fibers that are randomly interlaid, not in an identifiable manner as in a knitted fabric. Nonwoven webs include, for example, meltblown webs, spunbond webs, carded webs, wet-laid webs, airlaid webs, coform webs, hydraulically entangled webs, etc. The basis weight of the nonwoven web may generally vary, but is typically from about 5 grams per square meter ("gsm") to about 200 gsm, in some embodiments from about 10 gsm to about 150 gsm, and in some embodiments, from about 15 gsm to about 100 gsm.

As used herein, the term "meltblown" web or layer generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al.; U.S. Pat. No. 4,307,143 to Meitner, et al.; and U.S. Pat. No. 4,707,398 to Wisneski, et al., which are incorporated herein in their entirety by reference thereto for all purposes. Meltblown fibers may be substantially continuous or discontinuous, and are generally tacky when deposited onto a collecting surface.

As used herein, the term "spunbond" web or layer generally refers to a nonwoven web containing small diameter substantially continuous filaments. The filaments are formed by extruding a molten thermoplastic material from a plurality of fine, usually circular, capillaries of a spinnerette with the diameter of the extruded filaments then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond filaments are generally not tacky when they are deposited onto a collecting surface. Spunbond filaments may sometimes have diameters less than about 40 micrometers, and are often between about 5 to about 20 micrometers.

Detailed Description

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a substrate that contains a deodorizing ink. The ink contains carbonaceous particles (e.g., activated carbon) for adsorbing one or more malodorous compounds to reduce odor. Because carbonaceous particles typically have a dark black color that is sometimes aesthetically displeasing to the user, the deodorizing ink of the present invention also contains voided synthetic particles that mask, at least to some extent, the darker carbonaceous particles. More specifically, the voids of the particles contain air, which can scatter or diffract light to create an opaque effect that may hide the black color of the carbonaceous particles. In this manner, the color presented to the user may be more aesthetically pleasing. Various embodiments of the present invention will now be described in more detail.

I. Carbonaceous Particles

The carbonaceous particles may include activated carbon, carbon black, charcoal, etc. Activated carbon, for instance, may be derived from a variety of organic precursors such as bamboo, coconut shells, palm-kernel shells, wood chips, sawdust, corncob and seeds, etc. The carbonaceous particles may provide an increased surface area that enhances the adsorption of certain malodorous compounds. The carbonaceous particles may, for instance, have a specific surface area of at least about 200 $m^2/g$, in some embodiments at least about 500 $m^2/g$, and in some embodiments, at least about 1500 $m^2/g$. The term "specific surface area" was determined by the physical gas adsorption (B.E.T.) method of Bruanauer, Emmet, and Teller, Journal of American Chemical Society, Vol. 60, 1938, p. 309, with nitrogen as the adsorption gas.

To achieve the desired surface area, the carbonaceous particles generally have a small size. For example, the average size (e.g., diameter or width) of the carbonaceous particles may be from about 1 to about 100 micrometers, in some embodiments from about 5 to about 75 micrometers, and in some embodiments, from about 10 to about 50 micrometers. Without intending to be limited by theory, it is believed that particles having such a small size and high corresponding surface area may improve the adsorption capability for many malodorous compounds. The carbonaceous particles may also be porous. For example, the carbonaceous particles may have pores/channels with a mean diameter of greater than about 5 angstroms, in some embodiments greater than about 20 angstroms, and in some embodiments, greater than about 50 angstroms. Some suitable forms of carbonaceous particles and techniques for formation thereof are described in U.S. Pat. No. 5,693,385 to Parks; U.S. Pat. No. 5,834,114 to Economy, et al.; U.S. Pat. No. 6,517,906 to Economy, et al.; U.S. Pat. No. 6,573,212 to McCrae, et al., as well as U.S. Patent Application Publication Nos. 2002/0141961 to Falat, et al. and 2004/0166248 to Hu, et al., all of which are incorporated herein in their entirety by reference thereto for all purposes.

The concentration of carbonaceous particles in the deodorizing ink is generally tailored to facilitate odor control without adversely affecting other properties of the substrate. For instance, the carbonaceous particles may be present in the deodorizing ink (after drying) in an amount from about 10 wt. % to about 50 wt. %, in some embodiments from about 15 wt. % to about 45 wt. %, and in some embodiments, from about 20 wt. % to about 40 wt. %.

II. Voided Synthetic Particles

The voided synthetic particles have at least one void, but they may have multiple voids, interconnected voids, voids having channels connected to the outside of the particles, and they may encompass structures described as vesiculated and sponge-like. The void fraction of the particles may range from about 10% to about 75%, in some embodiments, from about 15% to about 70%, and in some embodiments, from about 25% to about 60%. The concentration of the voided synthetic particles in the deodorizing ink may vary depending on the nature of the particles, and the desired extent of odor control and color alteration. For instance, the voided synthetic particles may be present in the deodorizing ink (after drying) in an amount from about 5 wt. % to about 40 wt. %, in some embodiments from about 10 wt. % to about 35 wt. %, and in some embodiments, from about 15 wt. % to about 30 wt. %.

Voided synthetic particles having a size that is less than the size of the carbonaceous particles are typically more effective in accomplishing the desired masking function. Without intending to be limited by theory, it is believed that the small size allows for a greater number of voided particles per unit of area, which thus provides a better cumulative masking effect than would otherwise be provided by larger particles. Generally, such small voided synthetic particles have an average size of less than about 10 micrometers, in some embodiments less than about 5 micrometers, and in some embodiments, less than about 1 micrometer. For example, certain carbonaceous particles have an average size of approximately 35 micrometers. In such cases, the average size of the voided synthetic particles is typically less than about 35 micrometers, and preferably much smaller, such as less than about 1 micrometer. The shape of the voided synthetic particles may generally vary. In one particular embodiment, for instance, the voided synthetic particles are spherical in shape. However, it should be understood that other shapes are also contemplated by the present invention, such as plates, rods, discs, bars, tubes, irregular shapes, etc.

The material(s) that form the voided synthetic particles may vary. The voided synthetic particles may, for instance, be organic and/or inorganic in nature, and may be polymers, oligomers, molecules, and so forth. For example, the voided synthetic particles may be formed from polymers such as polystyrene, acrylic and/or (meth)acrylic polymers, acrylate and/or (meth)acrylate polymers, styrene/acrylic and/or styrene/(meth)acrylic copolymers, vinylidene chloride/acrylonitrile copolymers, etc. In one particular embodiment, the voided synthetic particles are formed from one or more latex polymers. Such voided latex polymers are generally prepared by swelling a core-shell emulsion polymer in such a way that one or more voids form in the interior of the particle that contribute to the opacity of the deodorizing ink. Such particles are typically prepared by swelling the core of the core-shell emulsion polymer, such as described in U.S. Pat. Nos. 4,427,836; 4,468,498; 4,594,363; 4,880,842; 5,494,971; 5,521,253; 5,157,084; 5,360,827; and 6,020,435, which are incorporated herein in their entirety by reference thereto for all purposes. Particularly suitable examples of core-shell voided synthetic particles are acrylic/styrene copolymer microspheres available from Rohm & Haas of Philadelphia, Pa. under the designations ROPAQUE™ (e.g., HP543, HP91 and HP1055).

The core polymer of the core-shell emulsion polymer may be obtained by a single stage process or a process involving several stages. In one embodiment, the core polymer is formed from an emulsion polymer that includes from 5% to 100%, based on the weight of the core polymer, of at least one hydrophilic monoethylenically unsaturated monomer and from 0% to 95%, based on the weight of the core polymer, of at least one nonionic monoethylenically unsaturated monomer. The hydrophilic monoethylenically unsaturated monomer may be polymerized alone or with the nonionic monoethylenically unsaturated monomer. Suitable hydrophilic monoethylenically unsaturated monomers may include monomers containing at least one carboxylic acid group, such as acrylic acid, methacrylic acid, acryloxypropionic acid, (meth)acryloxypropionic acid, itaconic acid, aconitic acid, maleic acid or anhydride, fumaric acid, crotonic acid, monomethyl maleate, monomethyl fumarate, monomethyl itaconate and so forth. Acrylic acid and methacrylic acid are particularly desired. If desired, the hydrophilic monoethylenically unsaturated monomer may also include a non-polymeric compound containing at least one carboxylic acid group that is absorbed into the core polymer before, during or after the polymerization of the hydrophobic shell polymer as a replacement for the hydrophilic monoethylenically unsaturated monomer in the hydrophilic core polymer. For example, suitable non-polymeric compounds may include $C_6$-$C_{12}$ aliphatic or aromatic monocarboxylic acids and dicarboxylic acids, such as benzoic acid, m-toluic acid, p-chlorobenzoic acid, o-acetoxybenzoic acid, azelaic acid, sebacic acid, octanoic acid, cyclohexanecarboxylic acid, lauric acid and monobutyl phthalate, and so forth. Suitable nonionic monoethylenically unsaturated monomers include styrene, a-methyl styrene, p-methyl styrene, t-butyl styrene, vinyltoluene, ethylene, vinyl acetate, vinyl chloride, vinylidene chloride, (meth)acrylonitrile, (meth)acrylamide, ($C_1$-$C_{20}$) alkyl or ($C_3$-$C_{20}$) alkenyl esters of (meth)acrylic acid, such as methyl(meth)acrylate, ethyl(meth)acrylate, butyl(meth)acrylate, 2-ethylhexyl(meth)acrylate, hydroxyethyl(meth)acrylate, hydroxypropyl(meth)acrylate, benzyl(meth)acrylate, lauryl(meth)acrylate, oleyl(meth)acrylate, palmityl(meth)acrylate, stearyl(meth)acrylate, and so forth.

In some cases, the core may also contain a polyethylenically unsaturated monomer. Suitable polyethylenically unsaturated monomers include comonomers containing at least two addition polymerizable vinylidene groups and are ethylenically unsaturated monocarboxylic acid esters of polyhydric alcohols containing 2-6 ester groups. Such comonomers include alkylene glycol diacrylates and dimethacrylates, such as for example, ethylene glycol diacrylate, ethylene glycol dimethacrylate, 1,3-butylene glycol diacrylate, 1,4-butylene glycol diacrylate propylene glycol diacrylate and triethylene glycol dimethylacrylate; 1,3-glycerol dimethacrylate; 1,1,1-trimethylol propane dimethacrylate; 1,1,1-trimethylol ethane diacrylate; pentaerythritol trimethacrylate; 1,2,6-hexane triacrylate; sorbitol pentamethacrylate; methylene bis-acrylamide, methylene bis-methacrylamide, divinyl benzene, vinyl methacrylate, vinyl crotonate, vinyl acrylate, vinyl acetylene, trivinyl benzene, triallyl cyanurate, divinyl acetylene, divinyl ethane, divinyl sulfide, divinyl ether, divinyl sulfone, diallyl cyanamide, ethylene glycol divinyl ether, diallyl phthalate, divinyl dimethyl silane, glycerol trivinyl ether, divinyl adipate; dicyclopentenyl(meth)acrylates; dicyclopentenyloxy (meth)acrylates; unsaturated esters of glycol monodicyclopentenyl ethers; allyl esters of α,β-unsaturated mono- and dicarboxylic acids having terminal ethylenic unsaturation including allyl methacrylate, allyl acrylate, diallyl maleate, diallyl fumarate, diallyl itaconate, and so forth.

If desired, the emulsion polymer may also contain an intermediate polymer that partially or fully encapsulates the core and itself is partially or fully encapsulated by the shell. The intermediate polymer may be prepared by emulsion polymerization in the presence of the core. The intermediate polymer may contain, for instance, from 0.3% to 20%, based on the weight of the intermediate polymer, of at least one hydrophilic monoethylenically unsaturated monomer, and from 80% to 99.7%, based on the weight of the intermediate polymer, of at least one nonionic monoethylenically unsaturated monomer. The hydrophilic monoethylenically unsaturated monomers and the nonionic monoethylenically unsaturated monomers useful for making the core are also useful for making the intermediate layer.

The shell polymer may be selected to provide a glass transition temperature ($T_g$) that is high enough to support the voids of the particle, e.g., such as greater than about 50° C., in some embodiments greater than about 60° C., and in some embodiments, greater than about 70° C. Such a polymer may be formed by emulsion polymerizing from 80% to 100%, based on the total weight of the shell, of at least one nonionic monoethylenically unsaturated monomer. The nonionic monoethylenically unsaturated monomers suitable for the core are also suitable for the shell. Styrene is particularly suitable. The shell may also contain from 0% to 20%, based on the weight of the shell, of one or more monoethylenically unsaturated monomers containing acid-functionality for making the hydrophobic polymer shell, such as acrylic acid, methacrylic acid, acryloxypropionic acid, (meth)acryloxypropionic acid, itaconic acid, aconitic acid, maleic acid, maleic anhydride, fumaric acid, crotonic acid, monomethyl maleate, monomethyl fumarate, monomethyl itaconate and so forth. Acrylic acid and methacrylic acid are particularly suitable. The shell is typically permeable to an aqueous or gaseous volatile or fixed basic swelling agent capable of swelling the core. Monomeric mixtures for making the shell may contain, for instance, from about 0.1% by weight to about 10% by weight, based on the total weight of the shell polymer, of an acid-functional monoethylenically unsaturated monomer.

To produce the void in the particles, the core is typically swelled with a swelling agent containing one or more volatile components. The swelling agent permeates the shell to swell the core. The volatile components of the swelling agent may then be removed by drying the latex particles, thereby causing a void to form within the latex particles. Although not required, the swelling agent may be an aqueous base. Examples of suitable aqueous bases include, but are not limited to, ammonia, ammonium hydroxide, alkali metal hydroxides, such as sodium hydroxide, or a volatile amine, such as trimethylamine or triethylamine. Removal of the templated core may also be accomplished in other ways, such as by calcining at elevated temperatures or by chemical reactions causing dissolution of the core material.

In addition to core-shell polymers, voided synthetic particles may also be formed using other well-known techniques. For example, U.S. Pat. No. 6,479,146 to Caruso, et al., which is incorporated herein in its entirety by reference thereto for all purposes, describes voided synthetic particles formed using electrostatic forces. In particular, voided synthetic particles are formed using colloid templated electrostatic layer-by-layer ("LBL") self-assembly of nanoparticle-polymer multilayers, followed by removal of the templated core. The template particles may, for instance, contain organic polymer lattices, such as polystyrene or styrene copolymer lattices. The template particles are alternately coated with polyelectrolyte molecules and nanoparticles. The polyelectrolytes are usually polymers having ionically dissociable groups that may be a component or substituent of the polymer chain. The nanoparticles are typically ceramic particles, such as silicon dioxide, titanium dioxide, and zirconium dioxide optionally doped with other metal oxides; magnetic particles, such as $Fe_3O_4$; magneto-optical particles; nitridic ceramic particles, such as $Si_3N_4$, carbidic ceramic particles; metallic particles, such as gold, silver, and palladium; and sulfur or selene-containing particles, such as cadmium sulfide, cadmium selenide etc. In one embodiment, the template particles are first coated with several layers of oppositely charged cationic and anionic polyelectrolytes before the alternating layers of nanoparticles and polyelectrolyte or the alternating nanoparticle layers are applied. The template particles may be coated with at least two and up to six layers of oppositely charged cationic and anionic polyelectrolytes, e.g., with three layers. The outermost polyelectrolyte layer may be oppositely charged with regard to the nanoparticle to be deposited. In most embodiments, the template particles are at least partially disintegrated after the process has been completed. They can be dissolved in appropriate solvents or thermally (e.g., by calcination to temperatures of at least about 500° C.). After dissolution of the template particles, voided shells remain that are composed of the nanoparticle material and optionally the polyelectrolyte material.

If desired, the electrostatically-formed particles may be modified to contain pores in at least one of the layers. Such pores can be formed by the polyelectrolytes or nanoparticles themselves. For instance, a high salt concentration of the medium used for the deposition of the polyelectrolyte may result in a high permeability of the shell wall. On the other hand, a high salt concentration of the medium used for the deposition of the nanoparticles (e.g., $SiO_2$) may results in a high packing density of the silica particles. Thus, by adjusting the salt concentrations in the deposition medium, the permeability of the shell can be controlled, as desired. Further, the permeability properties of the shell may be modified by selecting the conditions for decomposing the core, e.g., by selecting the temperature and heating conditions in a calcination procedure.

III. Other Components

The deodorizing ink may also contain a variety of optional components to assist in the application of the particles. Binders, for instance, may be employed to increase the durability of the deodorizing ink, even when present at high levels. The binder may also serve as an adhesive for bonding one substrate to another substrate. In addition to improving durability, the present inventor has also discovered that certain types of binders may provide properties to the resulting coated substrate. For instance, water-soluble organic polymers may be used as a binder in the present invention to improve drapability and residual odor. In addition, such water-soluble organic polymers may also provide a more aesthetically deodorizing ink than other types of binders. One suitable class of water-soluble organic polymers includes polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Suitable cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methylcellulose), METOLOSE Type SH (hydroxypropylmethyl cellulose), and METOLOSE Type SE (hydroxyethylmethyl cellulose). One particular example of a suitable nonionic cellulosic ether is ethyl hydroxyethyl cellulose having a degree of ethyl substitution (DS) of 0.8 to 1.3 and a molar substitution (MS) of hydroxyethyl of 1.9 to 2.9. The degree of ethyl substitution represents the average number of hydroxyl groups present on each anhydroglucose unit that have been reacted, which may vary between 0 and 3. The molar substitution represents the average number of hydroxyethyl groups that have reacted with each anhydroglucose unit. One such cellulosic ether is BERMOCOLL E 230FQ, which is an ethyl hydroxyethyl cellulose commercially available from Akzo Nobel. Other suitable cellulosic ethers are also available from Hercules, Inc. of Wilmington, Del. under the name "CULMINAL."

Another benefit of the water-soluble binder of the present invention is that it may facilitate the controlled release of the deodorizing ink from the substrate in an aqueous environment. Specifically, upon contacting an aqueous solution, the water-soluble binder dissolves and loses some of its binding qualities, thereby allowing other components of the deodorizing ink to be released from the substrate. This may be useful in various applications, such as for hard-surface wipers in which it is desired for the odor control components to be released into the wiped environment for sustained odor control. In other cases, however, it may be desired that the deodorizing ink remain adhered to the substrate, such as when the substrate is employed in certain types of absorbent articles. In such embodiments, it may be desired to employ a water-insoluble co-binder that does not substantially dissolve in an aqueous environment. Consequently, even upon dissolution of the water-soluble binder, the co-binder may help keep the components of the deodorizing ink adhered to the substrate. Suitable co-binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the co-binder. The polymer suitable for use in the lattices typically has a glass transition temperature of about 30° C. or less so that the flexibility of the resulting substrate is not substantially restricted. Moreover, the polymer also typically has a glass transition temperature of about −25° C. or more to minimize the tackiness of the polymer latex. For instance, in some embodiments, the polymer has a glass transition temperature from about −15° C. to about 15° C., and in some embodiments, from about −10° C. to about 0° C. For instance, some suitable polymer lattices that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer lattices described above may be readily varied, as is well known in the art, by utilizing a stabilizing agent having the desired charge during preparation of the polymer latex. Specific techniques for such polymer latex systems are described in more detail in U.S. Pat. No. 6,573,212 to McCrae, et al.

The total concentration of the binder and optional co-binder may generally vary depending on the desired properties of the resulting substrate. For instance, high total binder concentrations may provide better physical properties for the coated substrate, but may likewise have an adverse affect on other properties, such as the absorptive capacity of the substrate to which it is applied. Conversely, low total binder concentrations may not provide the desired degree of durability. Thus, in most embodiments, the total amount of binder employed in the deodorizing ink, including the water-soluble binder and any optional co-binder, is from about 1 wt. % to about 35 wt. %, in some embodiments from about 5 wt. % to about 30 wt. %, and in some embodiments, from about 10 wt. % to about 30 wt. %. To enhance the drapability and odor control properties of the substrate, the water-soluble binder typically constitutes at least about 50 wt. %, in some embodiments, at least about 75 wt. %, and in some embodiments, at least about 90 wt. % of the total amount of binder employed. Conversely, when utilized, the co-binder typically constitutes less than about 50 wt. %, in some embodiments less than about 25 wt. %, and in some embodiments, less than about 10 wt. % of the total amount of binder employed.

Colorants (e.g., pigments, dyes, etc.) may also be employed in the deodorizing ink of the present invention to improve its aesthetic appeal. Colorants may constitute from about 0.01 wt. % to about 40 wt. %, in some embodiments from about 1 wt. % to about 35 wt. %, and in some embodiments, from about 5 wt. % to about 30 wt. % of the deodorizing ink. If desired, the colorant may alternatively be applied separately from the deodorizing ink to present an aesthetically appealing contrast between the color of the deodorizing ink and the color of the colorant. For example, the colorant may be an inorganic and/or organic pigment. Some examples of commercially available organic pigments that may be used in the present invention include those that are available from Clariant Corp. of Charlotte, N.C., under the trade designations GRAPHTOL® or CARTAREN®. Other pigments, such as lake compounds (blue lake, red lake, yellow lake, etc.), may also be employed. Inorganic and/or organic dyes may also be utilized as a colorant. Exemplary organic dye classes include triarylmethyl dyes, monoazo dyes, thiazine dyes, oxazine dyes, naphthalimide dyes, azine dyes, cyanine dyes, indigo dyes, coumarin dyes, benzimidazole dyes, paraquinoidal dyes, fluorescein dyes, diazonium salt dyes, azoic diazo dyes, phenylenediamine dyes, diazo dyes, anthraquinone dyes, trisazo dyes, xanthene dyes, proflavine dyes, sulfonaphthalein dyes, phthalocyanine dyes, carotenoid dyes, carminic acid dyes, azure dyes, acridine dyes, and so forth. One particularly suitable class of dyes includes anthraquinone compounds, which may be classified for identification by their Color Index (CI) number. For instance, some suitable anthraquinones that may be used in the present invention, as classified by their "CI" number, include Acid Black 48, Acid Blue 25 (D&C Green No. 5), Acid Blue 40, Acid Blue 41, Acid Blue 45, Acid Blue 129, Acid Green 25, Acid Green 27, Acid Green 41, Mordant Red 11 (Alizarin), Mordant Black 13 (Alizarin Blue Black B), Mordant Red 3 (Alizarin Red S), Mordant Violet 5 (Alizarin Violet 3R), Natural Red 4 (Carminic Acid), Disperse Blue 1, Disperse Blue 3, Disperse Blue 14, Natural Red 16 (Purpurin), Natural Red 8, Reactive Blue 2, and so forth. One particularly suitable colorant is available from Akzo Nobel under the name "Hydrofilm 4000."

Still other compounds, such as surfactants, electrolytic salts, pH adjusters, etc., may also be included in the deodorizing ink of the present invention. Although not required, such additional components typically constitute less than about 5 wt. %, in some embodiments less than about 2 wt. %, and in some embodiments, from about 0.001 wt. % to about 1 wt. % of the deodorizing ink. For example, as is well known in the art, an electrolytic salt may be employed to control the gelation temperature of the water-soluble binder. Suitable electrolytic salts may include, but are not limited to, alkali halides or sulfates, such as sodium chloride, potassium chloride, etc.; alkaline halides or sulfates, such as calcium chloride, magnesium chloride, etc., and so forth.

IV. Substrate Application

As stated above, the deodorizing ink of the present invention is applied to a substrate. The substrate may function simply as a physical carrier for the deodorizing ink, or it may perform other functions of the article into which it is incorporated. To apply the deodorizing ink of the present invention to a substrate, the components are first typically dissolved or dispersed in a solvent to form an ink. For example, one or more of the above-mentioned components may be mixed with a solvent, either sequentially or simultaneously, to form an ink that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. The concentration of solvent in the ink is generally high enough to allow easy application, handling, etc. If the amount of solvent is too large, however, the amount of carbonaceous particles deposited on the substrate might be too low to provide the desired odor reduction. Although the actual concentration of solvent employed will generally depend on the type of particles and the substrate on which it is applied, it is nonetheless typically present in an amount from about 40 wt. % to about 99 wt. %, in some embodiments from about 50 to about 95 wt. %, and in some embodiments, from about 60 wt. % to about 90 wt. % of the ink.

The amount of the other components added to the ink may vary depending on the amount of odor reduction desired, the wet pick-up of the application method utilized, etc. For example, carbonaceous particles may constitute from about 0.01 wt. % to about 20 wt. %, in some embodiments from about 0.1 wt. % to about 15 wt. %, and in some embodiments, from about 0.5 wt. % to about 10 wt. % of the ink. Voided particles may constitute from about 0.01 wt. % to about 20 wt. %, in some embodiments from about 0.1 wt. % to about 15 wt. %, and in some embodiments, from about 0.5 wt. % to about 10 wt. % of the ink. A water-soluble organic polymer may constitute from about 0.01 wt. % to about 20 wt. %, in some embodiments from about 0.1 wt. % to about 15 wt. %, and in some embodiments, from about 0.5 wt. % to about 10 wt. % of the ink.

The solids content and/or viscosity of the ink may be varied to achieve the extent of odor reduction desired. For example, the ink may have a solids content of from about 1% to about 30%, in some embodiments from about 3% to about 25%, and in some embodiments, from about 5% to about 15%. By varying the solids content of the ink, the presence of carbonaceous particles, voided synthetic particles, and/or other components in the ink may be controlled. For example, to form an ink with a higher level of particles, the ink may be provided with a relatively high solids content so that a greater percentage of carbonaceous particles is incorporated into the ink during the application process. In addition, the viscosity of the ink may also vary depending on the application method and/or type of binder employed. For instance, lower viscosities may be employed for saturation coating techniques (e.g., dip-coating), while higher viscosities may be employed for drop-coating techniques. Generally, the viscosity is from about 500 to about $2 \times 10^6$ centipoise, such as measured with a Brookfield DV-1 viscometer with an LV spindle. If desired, thickeners or other viscosity modifiers may be employed in the ink to increase or decrease viscosity.

The ink may be applied to a substrate using any conventional technique, such as bar, roll, knife, curtain, print (e.g., rotogravure), spray, slot-die, or dip-coating techniques. The materials that form the substrate (e.g., fibers) may be coated before and/or after incorporation into the substrate. The ink may be applied to one or both surfaces of the substrate. For example, the ink is generally present on at least the surface of the substrate that is likely to contact the targeted odor during use. In addition, the ink may cover an entire surface of the substrate, or may only cover a portion of the surface. When applying the ink to multiple surfaces, each surface may be coated sequentially or simultaneously.

Regardless of the manner in which it is applied, the resulting substrate may be heated to a certain temperature to drive the solvent from the ink. For example, the substrate may be heated to a temperature of at least about 50° C., in some embodiments at least about 70° C., and in some embodiments, at least about 80° C. By minimizing the amount of solvent in the resulting deodorizing ink, a larger surface area of carbonaceous particles may be available for contacting odorous compounds, thereby enhancing odor reduction. It should be understood, however, that relatively small amounts of solvent may still be present in the deodorizing ink. For example, the deodorizing ink may contain a solvent in an amount less than about 0.5% by weight, in some embodiments less than about 0.1% by weight, and in some embodiments, less than about 0.01% by weight.

Generally speaking, any of a variety of different substrates may be incorporated with the deodorizing ink of the present invention. For instance, nonwoven webs, woven fabrics, knit fabrics, paper web, film, foams, etc., may be applied with the deodorizing ink. When utilized, the nonwoven webs may include, but are not limited to, spunbonded webs (apertured or non-apertured), meltblown webs, bonded carded webs, airlaid webs, coform webs, hydraulically entangled webs, and so forth. Typically, the polymers used to form the substrate have a softening or melting temperature that is higher than the temperature needed to remove the solvent from the ink. One or more components of such polymers may have, for instance, a softening temperature of from about 100° C. to about 400° C., in some embodiments from about 110° C. to about 300° C., and in some embodiments, from about 120° C. to about 250° C. Examples of such polymers may include, but are not limited to, synthetic polymers (e.g., polyethylene, polypropylene, polyethylene terephthalate, nylon 6, nylon 66, KEVLAR®), syndiotactic polystyrene, liquid crystalline polyesters, etc.); cellulosic polymers (softwood pulp, hardwood pulp, thermomechanical pulp, etc.); combinations thereof; and so forth.

The solids add-on level of the deodorizing ink may also be varied as desired. The "solids add-on level" is determined by subtracting the weight of the untreated substrate from the weight of the treated substrate (after drying), dividing this calculated weight by the weight of the untreated substrate, and then multiplying by 100%. One particular benefit of the present invention is that high solids add-on levels, and consequently high levels of odor control, may be achieved without a substantial sacrifice in durability of the deodorizing ink. In some embodiments, for example, the add-on level is at least about 5% to about 600%, in some embodiments from about 10% to about 500%, and in some embodiments, from about 20% to about 300%. The thickness of the deodorizing ink may also vary. For example, the thickness may range from about 0.001 millimeters to about 0.4 millimeters, in some embodiments, from about 0.01 millimeters to about 0.30 millimeters, and in some embodiments, from about 0.01 millimeters to about 0.20 millimeters. Such a relatively thin deodorizing ink may enhance the flexibility of the substrate, while still providing odor control.

To maintain absorbency, porosity, flexibility, and/or some other characteristic of the substrate, it may sometimes be desired to apply the deodorizing ink so as to cover less than 100%, in some embodiments from about 10% to about 80%, and in some embodiments, from about 20% to about 60% of the area of one or more surfaces of the substrate. For instance, in one particular embodiment, the deodorizing ink is applied to the substrate in a preselected pattern (e.g., reticular pattern, diamond-shaped grid, dots, and so forth). Although not required, such a patterned deodorizing ink may provide sufficient odor control without covering a substantial portion of the surface area of the substrate. This may be desired to optimize flexibility, absorbency, or other characteristics of the substrate. It should be understood, however, that the deodorizing ink may also be applied uniformly to one or more surfaces of the substrate. In addition, a patterned deodorizing ink may also provide different functionality to each zone. For example, in one embodiment, the substrate is treated with two or more patterns of coated regions that may or may not overlap. The regions may be on the same or different surfaces of the substrate. In one embodiment, one region of a substrate is coated with a first deodorizing ink, while another region is coated with a second deodorizing ink. Likewise, an article may contain a first coated substrate and a second coated substrate. In either case, one region or substrate may be configured to reduce one type of odor, while another region or substrate may be configured to reduce another type of odor. Alternatively, one region or substrate may possess a higher level of a deodorizing ink than another region or substrate to provide different levels of odor reduction.

The deodorizing ink of the present invention may be employed in a wide range of articles. If desired, the deodorizing ink may be used in one or more components of an absorbent article, such as in a liquid-permeable layer (e.g., bodyside liner, surge layer, etc.), a substantially liquid-impermeable layer, a breathable layer (e.g., outer cover, ventilation layer, baffle, etc.), absorbent core, elastic member, and so forth. Various absorbent article configurations are described, for instance, in U.S. Pat. No. 5,649,916 to DiPalma, et al.; U.S. Pat. No. 6,110,158 to Kielpikowski; U.S. Pat. No. 6,663,611 to Blaney, et al.; U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., as well as U.S. Patent Application Publication No. 2004/0060112 to Fell et al., all of which are incorporated herein in their entirety by reference thereto for all purposes.

The deodorizing ink of the present invention is versatile and may also be used with other types of articles of manufacture. For instance, the deodorizing ink may be used in air filters, such as house filters, vent filters, disposable facemasks, and facemask filters. Exemplary facemasks, for instance, are described and shown, for example, in U.S. Pat. Nos. 4,802,473; 4,969,457; 5,322,061; 5,383,450; 5,553,608; 5,020,533; 5,813,398; and 6,427,693, which are incorporated herein in their entirety by reference thereto for all purposes. In one embodiment, a substrate coated with the deodorizing ink of the present invention may be utilized as a filtration layer of the facemask. Filtration layers, such as meltblown nonwoven webs, spunbond nonwoven webs, and laminates thereof, are well known in the art.

In still other embodiments, the deodorizing ink may be employed in conjunction with a garment. For instance, garments, such as meat and seafood packing industry aprons/attire, grocery store aprons, paper mill aprons/attire, farm/dairy garments, hunting garments, etc., may be incorporated with the deodorizing ink of the present invention. As an example, hunters often wear garments that are camouflaged for the particular hunting environment. The deodorizing ink of the present invention may thus be used to form the camouflage pattern. Specifically, the deodorizing ink may impart the desired color pattern and also help reduce human odor during hunting.

The effectiveness of the deodorizing ink of the present invention may be measured in a variety of ways. For example, the percent of an odorous compound adsorbed by the deodorizing ink may be determined using the headspace gas chromatography test as set forth herein. In some embodiments, for instance, the deodorizing ink of the present invention is capable of adsorbing at least about 25%, in some embodiments at least about 45%, and in some embodiments, at least about 65% of a particular odorous compound. The effectiveness of the deodorizing ink in removing odors may also be measured in terms of "Relative Adsorption Efficiency", which is also determined using headspace gas chromatography and measured in terms of milligrams of odor adsorbed per gram of substrate or carbon. It should be recognized that the surface chemistry of any one type of deodorizing ink may not be suitable to reduce all types of odors, and that low adsorption of one or more odorous compounds may be compensated by good adsorption of other odorous compounds.

The present invention may be better understood with reference to the following examples.

Test Methods

Quantitative odor adsorption was determined using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig (188.9 kPa); headspace vial pressure: 15.8 psig (210.3 kPa); supply line pressure is at 60 psig (515.1 kPa). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

Operating Parameters for the Headspace Gas Chromatography Device
Headspace Parameters

| Zone Temps, ° C. | Oven | 37 |
|---|---|---|
|  | Loop | 85 |
|  | Transfer Line | 90 |
| Event Time, minutes | GC Cycle time | 10.0 |
|  | Vial eq. Time | 10.0 |
|  | Pressuriz. Time | 0.20 |
|  | Loop fill time | 0.20 |
|  | Loop eq. Time | 0.15 |
|  | Inject time | 0.30 |
| Vial Parameters | First vial | 1 |
|  | Last vial | 1 |
|  | Shake | [off] |

The test procedure involved placing 0.035 grams of fabric, depending on the level of deodorizing ink, in a 20-cubic centimeter headspace vial. Using a syringe, an aliquot of the odorous compound (3.6 microliters of dimethyl disulfide) was also placed in the vial. The vial was then sealed with a cap and a septum and placed in a headspace gas chromatography oven at 37° C. After ten minutes, a hollow needle was inserted through the septum and into the vial. A 1 cubic centimeter sample of the headspace (air inside the vial) was then injected into the gas chromatograph. The odor removing efficiency of the fabric was determined by comparing the peak area for DMDS in the chromatograph (retention time of 2.74 minutes) for the vials that contained fabric and DMDS relative to the vials that contained only DMDS.

EXAMPLE 1

Pieces (7"×10") of a 0.9 osy bonded carded web fabric (75% 3.0 denier FiberVisions ESC 215 bicomponent (PE sheath/PP core) fiber with 0.55% HR6 finish, 25% 6.0 denier Invista T-295 polyester fiber with 0.50% L1 finish) were coated on one side with a carbon ink using a #60 single wound metering rod. The ink was prepared as follows. In a 250 mL Pyrex® beaker, 1.8 grams of Bermocoll E230 FQ (an ethyl hydroxyethyl cellulose (EHEC) from Akzo Nobel) were added to 75.0 grams of stirring, warm (ca. 65° C.) distilled water. After about 5 minutes, the heat source (i.e., hot plate) was removed to allow the stirring liquid to cool. When the solution was cool (ca. 23° C.) and noticeably more clear and viscous, the other ingredients were added sequentially. The first additional component added to the stirring E230 FQ/water solution was 7.1 grams of ROPAQUE™ Ultra (a hollow-sphere styrene acrylic copolymer emulsion from Rohm and Haas Company, particle size of 0.4 micrometers, % solids measured at 29.3%), followed by 3.0 grams of Nuchar SA-1500 activated carbon powder (MeadWestvaco Corp., average particle size of 35 micron from scanning electron microscopy), 3.4 grams of Hydrofilm 4000 Cyan (Akzo Nobel, % solids measured at 45.5%), and 3.4 grams of Hydrofilm 4000 Opaque White (Akzo Nobel, % solids measured at 60.8%). The viscosity of the final ink was measured at about 800 centipoise using a Brookfield DV-I viscometer with a LV-2 spindle set at 20 rpm. The components of the ink are listed in the following table.

| Component | Calculated Amount (wt. %) |
|---|---|
| Activated Carbon | 3.2% |
| ROPAQUE ™ Ultra | 2.2% |
| Bermocoll E230 FQ | 1.9% |
| Hydrofilm 4000 Cyan | 1.6% |
| Hydrofilm 4000 Opaque White | 2.2% |
| Water | 88.9% |

The percent solids were measured at 11.1% using a Sartorius MA 30 analyzer. After applying the ink to the fabric surface, the coated fabric pieces were dried in a forced air oven at 110° C. for about 15-20 minutes. The solids add-on level was calculated from the initial fabric weight (1.5 grams) and the dry coated fabric weight (2.9±0.1 grams), and was determined to be approximately 93%. The total composition of the coated fabric is set forth below:

| % Fabric | % Activated Carbon | % ROPAQUE Ultra | % E230 FQ | % Hydrofilm 4000 Cyan | % Hydrofilm 4000 White |
|---|---|---|---|---|---|
| 52.5 ± 1.8 | 13.6 ± 0.5 | 9.4 ± 0.4 | 8.0 ± 0.3 | 7.0 ± 0.3 | 9.5 ± 0.4 |

Upon testing in the manner described above, it was determined that the coated fabric adsorbed 71±3 milligrams of DMDS per gram fabric and 534±20 per gram carbon.

EXAMPLE 2

Pieces (7"×10") of a 0.9 osy bonded carded web fabric (75% 3.0 denier FiberVisions ESC 215 bicomponent (PE sheath/PP core) fiber with 0.55% HR6 finish, 25% 6.0 denier Invista T-295 polyester fiber with 0.50% L1 finish) were coated on one side with a carbon ink using a #60 single wound metering rod. The ink was prepared as follows. In a 250 mL Pyrex® beaker, 1.8 grams of Bermocoll E230 FQ were added to 75.0 grams of stirring, warm (ca. 65° C.) distilled water. After about 5 minutes, the hot plate was removed to allow the stirring liquid to cool. When the solution was cool (ca. 23° C.) and noticeably more clear and viscous, the other ingredients were added sequentially. The first additional component added to the stirring E230 FQ/water solution was 6.6 grams of ROPAQUE™ Ultra, followed by 3.0 grams of bamboo charcoal powder (Taiwan Textile Research Institute, average particle size of 8.5 microns from scanning electron microscopy), 3.4 grams of Hydrofilm 4000 Cyan, and 3.5 grams of Hydrofilm 4000 Opaque White. The viscosity of the final ink was measured at about 600 centipoise using a Brookfield DV-I viscometer with a LV-2 spindle set at 20 rpm. The components of the ink are listed in the following table.

| Component | Calculated Amount (wt. %) |
| --- | --- |
| Bamboo charcoal | 3.2% |
| ROPAQUE™ Ultra | 2.1% |
| Bermocoll E230 FQ | 1.9% |
| Hydrofilm 4000 Cyan | 1.6% |
| Hydrofilm 4000 Opaque White | 2.3% |
| Water | 88.9% |

The percent solids were measured at 11.4% using a Sartorius MA 30 analyzer. After applying the ink to the fabric surface, the coated fabric pieces were dried in a forced air oven at 110° C. for about 20-30 minutes. The solids add-on level was calculated from the initial fabric weight (1.5 grams) and the dry coated fabric weight (2.7±0.1 grams), and was determined to be approximately 80%. The total composition of the coated fabric is set forth below:

| % Fabric | % Bamboo Charcoal | % ROPAQUE Ultra | % E230 FQ | % Hydrofilm 4000 Cyan | % Hydrofilm 4000 White |
| --- | --- | --- | --- | --- | --- |
| 55.6 ± 0.5 | 12.8 ± 0.2 | 8.3 ± 0.1 | 7.5 ± 0.1 | 6.6 ± 0.1 | 9.1 ± 0.1 |

The fabrics of Example 2 were a slightly darker blue color than the fabrics of Example 1, most likely due to the smaller particle size of the bamboo charcoal (8.5 microns) versus Nuchar SA-1500 activated carbon (35 microns). Upon testing in the manner described above, it was determined that the coated fabric adsorbed 22±1 milligrams of DMDS per gram fabric and 173±11 per gram carbon.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A substrate that contains a deodorizing ink, the deodorizing ink comprising from about 10 wt. % to about 50 wt. % carbonaceous particles and from about 5 wt. % to about 40 wt. % voided synthetic particles, wherein the voided synthetic particles have an average size less than the average size of the carbonaceous particles.

2. The substrate of claim 1, wherein the average size of the carbonaceous particles is from about 1 to about 100 micrometers.

3. The substrate of claim 1, wherein the average size of the carbonaceous particles is from about 5 to about 75 micrometers.

4. The substrate of claim 1, wherein the carbonaceous particles constitute from about 15 wt. % to about 45 wt. % of the ink.

5. The substrate of claim 1, wherein the average size of the voided synthetic particles is about 10 micrometers or less.

6. The substrate of claim 1, wherein the average size of the voided synthetic particles is about 1 micrometer or less.

7. The substrate of claim 1, wherein the voided synthetic particles constitute from about 10 wt. % to about 35 wt. % of the ink.

8. The substrate of claim 1, wherein the voided synthetic particles have a void fraction of from about 10% to about 75%.

9. The substrate of claim 1, wherein the voided synthetic particles are formed from a latex polymer.

10. The substrate of claim 9, wherein the latex polymer includes a styrene-acrylic copolymer.

11. The substrate of claim 1, wherein the voided synthetic particles are formed from a core polymer and a shell polymer.

12. The substrate of claim 11, wherein the shell polymer is formed from a nonionic monoethylenically unsaturated monomer, a monoethylenically unsaturated monomer containing acid functionality, or a combination thereof.

13. The substrate of claim 11, wherein the shell polymer includes a styrene-acrylic acid copolymer.

14. The substrate of claim 1, wherein the deodorizing ink further comprises a nonionic cellulosic ether.

15. The substrate of claim 14, wherein the nonionic cellulosic ether includes an alkyl hydroxyalkyl cellulose ether.

16. The substrate of claim 14, wherein the nonionic cellulosic ether comprises from about 1 wt. % to about 35 wt. % of the deodorizing ink.

17. The substrate of claim 1, wherein the solids add-on level of the ink is from about 10% to about 500%.

18. The substrate of claim 1, wherein the deodorizing ink further comprises a colorant.

19. The substrate of claim 1, wherein the substrate contains a nonwoven web, film, or a combination thereof.

20. A personal care absorbent article that comprises the substrate of claim 1.

21. A nonwoven web that contains a deodorizing ink, the deodorizing ink comprising from about 10 wt. % to about 50 wt. % activated carbon particles and from about 5 wt. % to about 40 wt. % voided latex particles, wherein the carbonaceous particles have an average size of from about 5 to about 75 micrometers and the voided latex particles have an average size of about 5 micrometers or less.

22. The nonwoven web of claim 21, wherein the carbonaceous particles constitute from about 15 wt. % to about 45 wt. % of the ink.

23. The nonwoven web of claim 21, wherein the average size of the voided latex particles is about 1 micrometer or less.

24. The nonwoven web of claim 21, wherein the voided latex particles constitute from about 10 wt. % to about 35 wt. % of the ink.

25. The nonwoven web of claim 21, wherein the voided latex particles have a void fraction of from about 10% to about 75%.

26. The nonwoven web of claim 21, wherein the voided latex particles are formed from a styrene-acrylic copolymer.

27. The nonwoven web of claim 21, wherein the voided latex particles are formed from a core polymer and a shell polymer.

28. The nonwoven web of claim 27, wherein the shell polymer is formed from a nonionic monoethylenically unsaturated monomer, a monoethylenically unsaturated monomer containing acid functionality, or a combination thereof.

29. The nonwoven web of claim 27, wherein the shell polymer includes a styrene-acrylic acid copolymer.

30. The nonwoven web of claim 21, wherein the deodorizing ink further comprises a nonionic cellulosic ether.

31. The nonwoven web of claim 21, wherein the solids add-on level of the ink is from about 10% to about 500%.

32. The nonwoven web of claim 21, wherein the deodorizing ink further comprises a colorant.

* * * * *